(12) United States Patent
Fu et al.

(10) Patent No.: US 7,126,016 B2
(45) Date of Patent: Oct. 24, 2006

(54) PROCESS FOR PREPARING FLUOROCARBOXYLIC ACIDS

(75) Inventors: Ta-Wei Fu, Vienna, WV (US); Steven H. Swearingen, Wilmington, DE (US); Takuya Ichida, Settsu (JP); Shuji Itatani, Settsu (JP)

(73) Assignees: E.I. DuPont De Nemours and Company, Wilmington, DE (US); Daikin Industries, Ltd., Osaka (JP)

( * ) Notice: Subject to any disclaimer, the term of this patent is extended or adjusted under 35 U.S.C. 154(b) by 43 days.

(21) Appl. No.: 11/088,465

(22) Filed: Mar. 24, 2005

(65) Prior Publication Data
US 2005/0171381 A1 Aug. 4, 2005

Related U.S. Application Data

(63) Continuation of application No. PCT/US2003/028548, filed on Sep. 29, 2003.

(60) Provisional application No. 60/414,421, filed on Sep. 30, 2002.

(51) Int. Cl.
*C07C 51/00* (2006.01)

(52) U.S. Cl. ........................ 554/154; 554/156

(58) Field of Classification Search ........... 554/154, 554/156
See application file for complete search history.

(56) References Cited

U.S. PATENT DOCUMENTS

| 3,227,736 A | 1/1966 | Tschesche et al. ....... 260/405.5 |
| 5,196,579 A | 3/1993 | Gries et al. ................. 562/580 |
| 6,013,795 A | 1/2000 | Manzara et al. ........... 544/106 |
| 6,248,923 B1 | 6/2001 | Lin et al. .................... 562/892 |

FOREIGN PATENT DOCUMENTS

| WO | WO 02/16302 A1 | 2/2002 |
| WO | WO 2004/029008 A2 | 4/2004 |

OTHER PUBLICATIONS

Supplementary European Search Report dated May 23, 2006 for EP 03799283.1.
International Search Report dated May 11, 2004 for PCT/US2003/026306.
International Search Report dated Jul. 2, 2004 for PCT/US2003/028548.

*Primary Examiner*—Deborah D. Carr
(74) *Attorney, Agent, or Firm*—Kilyk & Bowersox, P.L.L.C.

(57) ABSTRACT

A fluorocarboxylic acid preparation process continuously carries out acidification reaction treatment and washing treatment, and includes subjecting a fluorocarboxylate-containing aqueous solution to acidification reaction treatment in the presence of sulfuric acid so as to form a sulfate-containing fluorocarboxylic acid phase; and subjecting the fluorocarboxylic acid phase to washing treatment using an aqueous sulfuric acid solution.

13 Claims, 1 Drawing Sheet

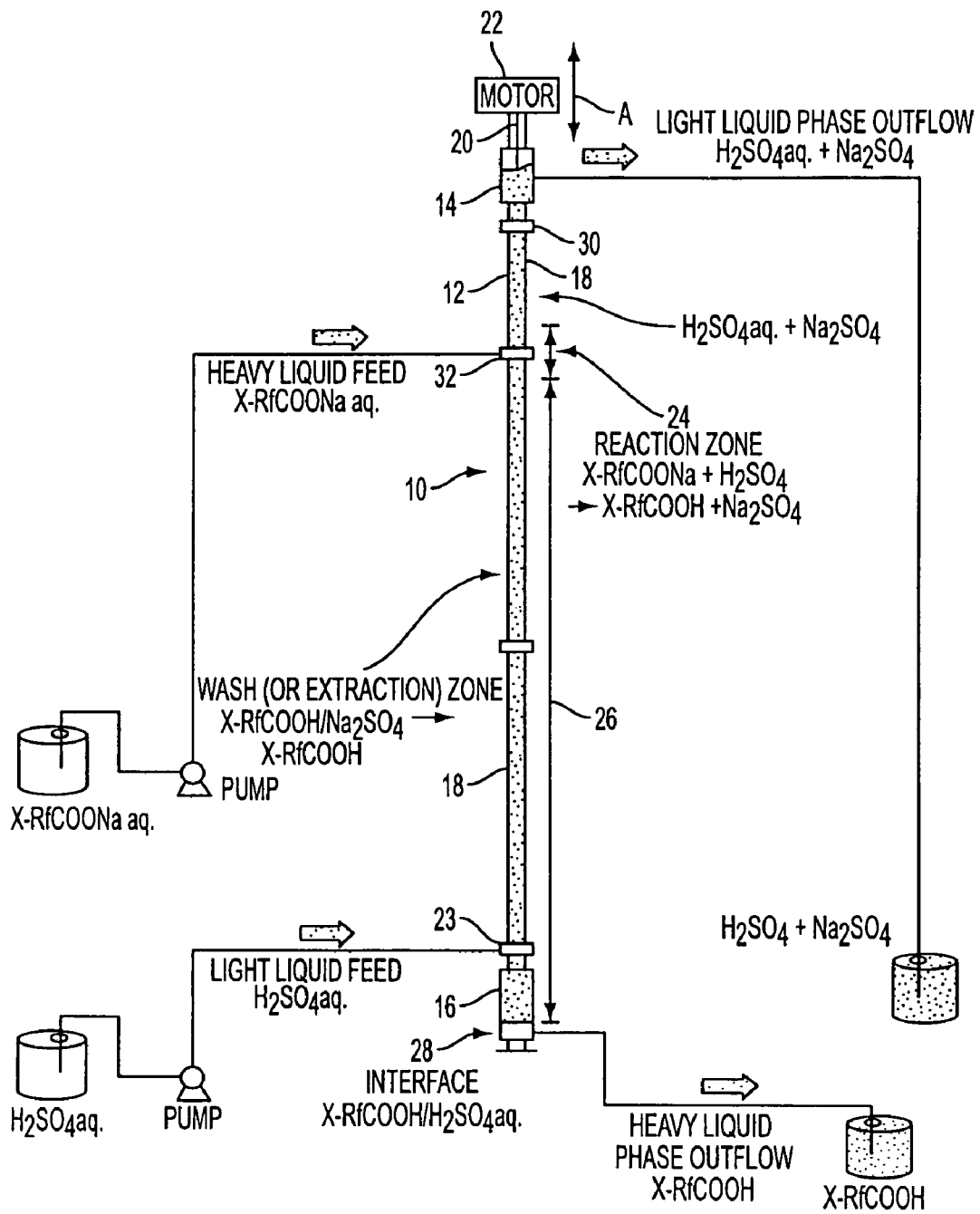

PROCESS FOR PREPARING FLUOROCARBOXYLIC ACIDS

CROSS REFERENCE TO RELATED APPLICATIONS

The present application is a continuation of International Patent Application No. PCT/US2003/028548, filed Sep. 29, 2003, which in turn claims priority from U.S. Provisional Application No. 60/414,421 filed Sep. 30, 2002, incorporated herein by reference.

BACKGROUND OF THE INVENTION

1. Field of the Invention

The present invention relates to a process for preparing fluorocarboxylic acids. More particularly, it relates to a process for preparing fluorocarboxylic acids in high purity and in high yield from fluorocarboxylates. The invention relates specifically to a process for preparing $C_{4-14}$, and especially $C_{7-9}$, fluorocarboxylic acids, including fluoroalkylcarboxylic acids, and particularly perfluoroalkylcarboxylic acids.

2. Description of the Related Art

Fluorocarboxylic acids, such as $C_8$ fluorocarboxylic acids and their salts, are known to have good surface activity. These fluorocarboxylic acids, as well as ammonium salts and alkali metal salts thereof, are widely used as polymerization emulsifying agents in the polymerization of fluoroolefins such as tetrafluoroethylene. Moreover, given the generally high cost of such fluorocompounds and their impact on the environment, it is desirable that they be recovered, purified and reused to the greatest possible extent.

One method that has been proposed for recovering and purifying such fluorocompounds involves preparing (or regenerating) fluorocarboxylic acid from a fluorocarboxylate-containing aqueous solution. In this method, in a tank-type reactor, sulfuric acid is used to carry out an acidification reaction on a fluorocarboxylate-containing aqueous solution, giving an acidification solution. Next, the acidification solution is heated and then liquid layers are separated to obtain a fluorocarboxylic acid-containing organic phase and an aqueous phase. The organic phase is recovered, then washed with an aqueous sulfuric acid solution to recover the fluorocarboxylic acid. If necessary, the recovered fluorocarboxylic acid is subsequently purified by distillation (see U.S. Pat. No. 6,281,374).

One problem with this related art method is the loss of fluorocarboxylic acid with liquid-liquid separation following the acidification reaction. Moreover, this related art process uses as the starting material an aqueous solution having a fluorocarboxylate concentration of about 5 to 40 wt %, preferably 5 to 30 wt %, more preferably 10 to 20 wt %. If the fluorocarboxylate concentration is below the desired range within the limits disclosed above, the solution can be concentrated by evaporation or other means.

As can be seen from the above, related art processes give rise to a loss of fluorocarboxylic acid. Moreover, in cases where the fluorocarboxylic acid preparation process includes enrichment, acidification, liquid-liquid separation and subsequent recovery, it is not easy to make the production process continuous.

SUMMARY OF THE INVENTION

It is therefore an object of the present invention to provide a process for the continuous production of high-purity fluorocarboxylic acids in an economically beneficial manner, which process mitigates, and preferably eliminates, at least one of the aforementioned problems associated with related art processes for preparing fluorocarboxylic acids from fluorocarboxylates. Moreover, because fluorocarboxylic acids generally are not biodegradable, to protect the global environment, it is important to minimize the release of fluorocarboxylic acid outside the production process system. Accordingly, it is also an object of the invention to provide a process for efficiently preparing fluorocarboxylic acid which reduces loss from the production system to a greater extent than the related art production process described above.

We have found that the above objects can be achieved with a process for preparing fluorocarboxylic acid in which acidification reaction treatment and washing treatment are continuously carried out, which process includes the steps of subjecting a fluorocarboxylate-containing aqueous solution to acidification reaction treatment in the presence of sulfuric acid so as to form a sulfate-containing fluorocarboxylic acid phase; and subjecting the fluorocarboxylic acid phase to washing treatment using an aqueous sulfuric acid solution.

BRIEF DESCRIPTION OF THE DRAWING

The figure is a schematic flow sheet illustrating the fluorocarboxylic acid preparation process of the invention using a Karr column.

Reference symbols used in the figure are explained as follows:

10: Karr column
12: Cylindrical section
14, 16: Decanters
18: Plate
20: Shaft
22: Motor
23: Bottom end of cylindrical section
24: Reaction zone
26: Washing zone
28: Interface
30: Top end of cylindrical section
32: Heavy liquid feed opening

DETAILED DESCRIPTION OF THE INVENTION

In the inventive process, the term "continuously" means that, instead of collecting all the fluorocarboxylic acid phase obtained by acidification reaction treatment and then subjecting the collected fluorocarboxylic acid phase to washing treatment, i.e., carrying out acidification reaction treatment and washing treatment independently (that is, separately), the fluorocarboxylic acid phase obtained by acidification reaction treatment is successively washed and, even as such washing treatment is taking place, the fluorocarboxylate-containing aqueous solution is newly subjected to acidification treatment. Therefore, the fluorocarboxylate-containing aqueous solution is continuously fed to a process which carries out the preparation method and is continuously subjected to acidification treatment, thereby continuously obtaining a fluorocarboxylic acid phase, which phase is then continuously subjected to washing treatment, thereby continuously obtaining a washed fluorocarboxylic acid phase.

In the aforementioned washing treatment, at least some of the compounds (e.g., sulfate) which are present in the fluorocarboxylic acid phase obtained by acidification reaction treatment and can be taken up by an aqueous sulfuric acid solution are removed from the fluorocarboxylic acid phase.

In the preparation process of the invention, the fluorocarboxylate present in the aqueous solution is acidified by acidification reaction treatment. "Acidification reaction," as used herein, refers to the reaction which converts by means of sulfuric acid the fluorocarboxylate present in the aqueous solution to the corresponding fluorocarboxylic acid. Sulfate forms as a by-product of this reaction.

The fluorocarboxylate preferably is a compound having the general formula

$$X\text{—}RfCOOM \qquad (1).$$

In the formula, X is a hydrogen atom, a fluorine atom or a chlorine atom; M is a monovalent alkali metal ion, preferably sodium or potassium, or ammonium ion; and Rf is a linear or branched fluoroalkyl group of 4 to 14 carbons, and preferably 7 to 9 carbons, such as 7 carbons, and especially a linear or branched perfluoroalkyl group.

Therefore, the fluorocarboxylic acid prepared by the acidification reaction has the general formula

$$X\text{—}RfCOOH \qquad (2).$$

In the formula, X and Rf are as defined above. In the inventive process, especially preferred examples are those in which the fluorocarboxylic acid is a perfluoroalkylcarboxylic acid such as $C_7F_{15}COOH$ and $C_8F_{17}COOH$, and the corresponding fluorocarboxylate is a perfluoroalkylcarboxylate such as $C_7F_{15}COONa$, $C_7F_{15}COONH_4$, $C_8F_{17}COONa$ and $C_8F_{17}COONH_4$.

In the inventive process, the fluorocarboxylate and the fluorocarboxylic acid mutually correspond. The term "correspond," as used in connection with these compounds, means that the group X—Rf— remains unchanged before and after the acidification reaction.

According to another embodiment of the invention, the fluorocarboxylate which is hydrolyzed is a compound having the general formula

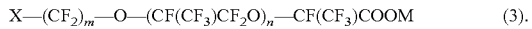

$$X\text{—}(CF_2)_m\text{—}O\text{—}(CF(CF_3)CF_2O)_n\text{—}CF(CF_3)COOM \qquad (3).$$

In the formula, X is a hydrogen atom, a fluorine atom or a chlorine atom; M is a monovalent alkali metal ion, preferably sodium or potassium, or ammonium ion; m is an integer from 1 to 10, such as 5; and n is an integer from 0 to 5, such as 1.

Therefore, the corresponding fluorocarboxylic acid prepared in this embodiment is a compound having the general formula

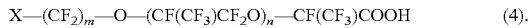

$$X\text{—}(CF_2)_m\text{—}O\text{—}(CF(CF_3)CF_2O)_n\text{—}CF(CF_3)COOH \qquad (4).$$

In the formula, X, m and n are as defined above.

In the process of the invention, acidification reaction treatment of the fluorocarboxylate-containing aqueous solution causes the fluorocarboxylate dissolved in the aqueous solution serving as the starting material to be acidified, thereby forming the corresponding fluorocarboxylic acid. In the presence of sulfuric acid, this fluorocarboxylic acid has a very low solubility in water. Accordingly, the fluorocarboxylic acid which forms as a result of acidification reaction treatment of the fluorocarboxylate dissolved within the aqueous phase appears in the form of a fluorocarboxylic acid phase as an organic phase separate and distinct from the aqueous phase, and that exists as a dispersed phase within the aqueous phase. The aqueous phase originates from the fluorocarboxylate-containing aqueous solution. In cases where the sulfuric acid present at the time of the acidification reaction is used in the form of an aqueous solution, the water present in the aqueous sulfuric acid solution also makes up the aqueous phase.

In addition to fluorocarboxylic acid, the fluorocarboxylic acid phase includes other compounds which may be present in the zone where the acidification reaction occurs (also referred to as the "reaction zone"), such as sulfate, water, and unreacted fluorocarboxylate. In cases where additional other compounds (e.g., hydrogen fluoride) are present in the starting material, such additional other compounds may also be present in the fluorocarboxylic acid phase. These other compounds and additional other compounds are generally present in a dissolved state, although they may in some cases be present in tiny liquid droplets of aqueous phase dispersed within the fluorocarboxylic acid phase. The sulfate that arises due to the acidification reaction readily dissolves in water, although a considerable amount is also present within the fluorocarboxylic acid phase. To remove at least part, and preferably substantially all, of the sulfate, as will be described subsequently, the fluorocarboxylic acid phase obtained by acidification reaction treatment is subjected to washing treatment. The various other compounds present in the fluorocarboxylic acid phase, if soluble in the aqueous sulfuric acid solution, also are at least partly removed by the washing treatment.

In the inventive process, the fluorocarboxylate acidification reaction in the presence of sulfuric acid, and thus (because water is present in the starting material) in the presence of an aqueous sulfuric acid solution, may be carried out under any suitable conditions and using any suitable apparatus, provided the fluorocarboxylic acid that forms exists in a liquid state. Generally, the reaction is carried out at a temperature higher than the melting point of the fluorocarboxylic acid which forms, typically a temperature at least about 3° C. higher, and preferably a temperature at least about 5° C. higher, such as a temperature from about 5 to 15° C. higher. The acidification reaction in the present invention, when carried out in the presence of sulfuric acid, can achieve a conversion (based on the fluorocarboxylate) close to substantially 100% in a relatively short reaction time. For example, in the preparation of linear $C_7F_{15}COOH$ (melting point, 53° C.), a conversion of substantially 100% can be achieved when the acidification reaction is carried out for a period of 2 to 5 minutes at 60 to 70° C.

In the inventive process, the acidification reaction can be started in, for example, sulfuric acid (concentrated sulfuric acid) or an aqueous sulfuric acid solution, and by continuously feeding the fluorocarboxylate-containing aqueous solution to a reactor. Thereafter, as the reaction proceeds, the fluorocarboxylic acid phase appears as the dispersed phase. More particularly, the acidification reaction can be carried out by mixing the fluorocarboxylate-containing aqueous solution and the sulfuric acid or aqueous sulfuric acid solution for a given length of time. As the acidification reaction proceeds, the fluorocarboxylic acid phase appears in the state of a mixture dispersed within the aqueous phase. This mixture includes overall the reaction products (fluorocarboxylic acid, sulfate), unreacted fluorocarboxylate, surplus sulfuric acid, and inert substances (such as impurities present in water and the reaction feedstock). When the mixture is left at rest following a given reaction period, the fluorocarboxylic acid phase (organic phase) and the aqueous phase separate. The fluorocarboxylic acid phase is then removed and collected. According to another embodiment, the fluorocarboxylic acid phase may be obtained in a form which contains some aqueous phase, or may even be obtained as a mixture of organic phase and aqueous phase with no liquid separation whatsoever. This type of fluorocarboxylic acid phase is continuously furnished to the subsequent washing treatment operation.

The apparatus used in the acidification reaction may generally be any suitable apparatus which is capable of continuously mixing the aqueous solution of fluorocarboxylate with sulfuric acid (concentrated sulfuric acid) or an aqueous sulfuric acid solution and carrying out the reaction for a given length of time, then continuously placing the mixture at rest and continuously obtaining a fluorocarboxylic acid phase. In an especially preferred embodiment, use is made of a mixing tank and liquid separation tank set called a mixer-settler, and preferably a plurality of such sets. According to another embodiment, a tube-type reactor may be used. The tube-type reactor may be a parallel current type or a countercurrent type reactor.

In the process of the invention, at all stages of the reaction (following formation by the reaction, and up to completion of a predetermined reaction time), the fluorocarboxylic acid phase generally has a higher specific gravity than the aqueous phase, and two phases—an organic phase and an aqueous phase—are present. Thus, when a tubular reactor is used, it is preferable for the reactor to be in the form of a column-type reactor. Countercurrent operation (i.e., with the direction of the stream of fluorocarboxylic acid phase which forms and the direction of the stream of aqueous sulfuric acid solution mutually opposed) is especially preferred.

The sulfuric acid concentration in the acidification reaction is generally about 2 to 95 wt %, preferably about 5 to 50 wt %, more preferably about 10 to 30 wt %, and most preferably about 15 to 20 wt %. This sulfuric aid concentration is the concentration of sulfuric acid within the aqueous phase in the acidification reaction. The density of the aqueous solution of fluorocarboxylate is taken into consideration in choosing the concentration of sulfuric acid. The density of the aqueous solution of fluorocarboxylate should be greater than the density of the sulfuric acid solution, particularly for the continuous countercurrent process described below. The amount and concentration of sulfuric acid (or aqueous sulfuric acid solution) used in the acidification reaction is selected so as to result in such a sulfuric acid concentration. As the reaction proceeds, sulfuric acid is consumed, but the sulfuric acid concentration within the aqueous phase is maintained within the above concentration range until completion of the reaction time. Accordingly, regardless of the sulfuric acid concentration, the acidification reaction is carried out under the condition that sulfuric acid is present in the aqueous phase until completion of the reaction time.

The aqueous solution of fluorocarboxylate subjected to acidification reaction treatment is not subject to any particular limitation, so long as the corresponding fluorocarboxylic acid is obtained by working the inventive process. Preferred fluorocarboxylates include those having 5 to 15 carbons, and preferably 8 to 10 carbons, such as 8 or 9 carbons. Fluoroalkylcarboxylates (e.g., ammonium salts, sodium salts) are especially preferred. The fluoroalkyl group may be a perfluoroalkyl group or a fluoroalkyl group in which at least one of the fluorines is substituted with hydrogen or chlorine. The fluoroalkyl group may be linear or branched.

The aqueous solution of fluorocarboxylate which is subjected to acidification reaction treatment may be obtained from any source. For example, it may be an aqueous solution formed by a method in which dilute wastewater containing fluorocarboxylate is recovered using a reverse osmosis membrane or an ion-exchange resin. The aqueous solution of fluorocarboxylate may contain also other constituents (e.g., hydrogen fluoride), provided they do not have an adverse effect on the inventive process.

As mentioned above, the sulfate (e.g., ammonium sulfate, sodium sulfate) that forms as a result of the acidification reaction is readily taken up by the aqueous phase even during the acidification reaction. Yet, following the acidification reaction, not all of the sulfate has been taken into the aqueous phase; some of it remains in the fluorocarboxylic acid phase. As a result, the fluorocarboxylic acid phase obtained from the acidification reaction, whether it is made up solely of this phase or also has some aqueous phase dispersed therein, includes sulfate that has formed. Therefore, in the process of the invention, the fluorocarboxylic acid phase is washed with an aqueous sulfuric acid solution to remove some, and preferably substantially all, of the sulfate present in the fluorocarboxylic acid phase, and thus improve the purity of the fluorocarboxylic acid. If liquid-liquid separation is not carried out after the acidification reaction, the resulting fluorocarboxylic acid phase is in the form of a mixture with the aqueous phase. Even in this case, by furnishing the mixture to washing treatment, the aqueous phase is taken up into and unites with the aqueous sulfuric acid solution. As a result, the aqueous phase is removed from the mixture and the sulfate present in the fluorocarboxylic acid phase transfers into the aqueous sulfuric acid solution.

Such washing treatment is an operation in which sulfate present in the fluorocarboxylic acid phase is extracted by the aqueous sulfuric acid solution. If the fluorocarboxylic acid phase also contains some aqueous phase, the wash is an operation which allows the aqueous phase to coalesce with the aqueous sulfuric acid solution. Such washing treatment is carried out by continuously mixing the continuously obtained fluorocarboxylic acid phase and the aqueous sulfuric acid solution. As with the acidification reaction, such mixture is carried out at a higher temperature than the melting point of the fluorocarboxylic acid, generally a temperature at least about 3° C. higher, and preferably a temperature at least about 5° C. higher, such as a temperature about 5 to 15° C. higher. For example, in the preparation of linear $C_7F_{15}COOH$ (melting point, 53° C.), washing is carried out at about 60 to 70° C.

In the inventive process, washing treatment proceeds at all stages in a liquid (aqueous phase)-liquid (organic phase) heterophase dispersed system.

(1) At the initial stage of washing treatment, an aqueous phase containing sulfuric acid and a fluorocarboxylic acid phase containing fluorocarboxylic acid and sulfate are present. These are mixed and brought into mutual contact, starting the wash in which the sulfate transfers from the fluorocarboxylic acid phase to the aqueous phase.

(2) At the completion of washing treatment, a fluorocarboxylic acid phase composed primarily of fluorocarboxylic acid and containing substantially no sulfate, and an aqueous phase containing sulfuric acid and sulfate are present.

In this type of washing treatment, good separation occurs between the aqueous phase and the fluorocarboxylic acid phase. When the system is placed at rest following mixture, an interface soon forms between the phases, and liquid separation occurs.

The sulfuric acid concentration of the aqueous sulfuric acid solution used for washing is generally about 2 to 95 wt %, preferably 5 to 50 wt %, more preferably about 10 to 30 wt %, and most preferably about 15 to 20 wt %. As used herein, "the sulfuric acid concentration of the aqueous sulfuric acid solution used for washing" can be thought of as referring to, at the start of washing, the sulfuric acid concentration in the aqueous sulfuric acid solution supplied for washing, and as referring to, after washing has begun, the concentration in the aqueous phase. This is because, in washing treatment, sulfuric acid does transfer to the fluorocarboxylic acid phase without being converted into another compound, but the amount of such sulfuric acid is not all that large. The sulfuric acid concentration need not necessarily remain constant throughout washing, although the aqueous sulfuric acid concentration actually does not change very much during washing treatment. By means of such washing treatment, there is obtained a fluorocarboxylic acid phase containing less sulfate, and an aqueous sulfuric acid solution phase, or aqueous phase, in which that sulfate has been taken up.

Such washing treatment is carried out using an aqueous sulfuric acid solution, giving a sulfuric acid-containing aqueous phase. Because acidification reaction treatment is carried out in the presence of sulfuric acid, the aqueous phase already used in washing treatment can be employed as the source of the sulfuric acid used in acidification reaction treatment. The aqueous phase that forms during acidification reaction treatment contains sulfate. On the other hand, the aqueous phase present in the acidification reaction treatment contains sulfuric acid, and so can be directly used in washing, in which case the aqueous sulfuric acid solution used in washing will contain sulfate. The latter embodiment can be carried out by, after the acidification reaction, taking up (i.e., extracting) the sulfate that has formed into the aqueous phase present in the reaction zone, so that washing is in fact achieved by the transfer of sulfate from the fluorocarboxylic acid phase (higher sulfate concentration) to the aqueous phase present around it (lower sulfate concentration) at the time of the reaction.

The amount of aqueous sulfuric acid solution used in washing may be suitably selected according to the amount of fluorocarboxylic acid phase to be washed, and particularly the amount of sulfate present therein. Washing is carried out at a weight ratio of the amount of aqueous sulfuric acid solution used (S) to the amount of fluorocarboxylic acid phase to be washed (F), or S/F, in a range of generally about 0.2 to 5, preferably about 0.5 to 3, and most preferably about 1 to 2. This ratio S/F is based on the amounts S and F fed to the washing operation, although it is preferable for the above range to be maintained during washing as well. Actually, the absolute amount of sulfate removed by washing is not large, and so the S/F ratio does not change much during washing. Industrially, the amount of fluorocarboxylic acid phase (F) to be washed may be regarded as substantially the same as the amount of fluorocarboxylate included in the aqueous solution furnished to acidification reaction treatment.

In washing treatment, the fluorocarboxylic acid phase and the aqueous sulfuric acid solution are mixed, then allowed to rest to permit the fluorocarboxylic acid phase composed primarily of fluorocarboxylic acid and the aqueous phase composed primarily of sulfuric acid and water to separate into two phases, after which the organic phase is removed and collected. This process is carried out continuously. The organic phase and the aqueous phase are in equilibrium at the liquid separation conditions. Therefore, the fluorocarboxylic acid phase contains amounts of water, sulfuric acid and sulfate corresponding to their saturation solubilities at the liquid separation conditions, but the amounts of sulfuric acid and sulfate are both very small and the amount of water is small. If necessary, the amount of sulfate contained can be reduced by subjecting the fluorocarboxylic acid phase that has been collected to another wash with aqueous sulfuric acid solution. Accordingly, in the inventive process, it is possible by means of washing to obtain fluorocarboxylic acid (strictly speaking, water-containing fluorocarboxylic acid) in which the sulfate concentration has been reduced, and preferably from which the sulfate has been substantially eliminated. Depending on its intended use, the fluorocarboxylic acid thus obtained may be used directly without further treatment. As in the case of the acidification reaction, when the system is placed at rest following mixture during the washing operation, liquid separation between the fluorocarboxylic acid phase and the aqueous sulfuric acid solution phase is good. Moreover, the amount of fluorocarboxylic acid present in the aqueous phase is low.

For example when $C_7F_{15}COOH$ and a 15 wt % aqueous sulfuric acid solution are mixed in a 1:1 weight ratio, then subjected to liquid separation, the sulfuric acid present in the organic $C_7F_{15}COOH$ phase is only about 4,000 ppm by weight (amount in the $C_7F_{15}COOH$ solid). At this sulfuric acid concentration, depending on the intended use of the $C_7F_{15}COOH$, additional purification steps can often be omitted. The $C_7F_{15}COOH$ concentration in the aqueous sulfuric acid solution phase (aqueous phase) is less than 100 ppm by weight. This means that the loss of fluorocarboxylic acid present in the aqueous phase discarded as process wastewater can be minimized.

The washing operation is a type of extraction operation in which sulfate present in the fluorocarboxylic acid phase is transferred to the aqueous phase. Here too, as in the acidification reaction treatment described above, efficient contact between both phases present is desirable. Accordingly, as in a continuous extraction operation, washing treatment can be carried out continuously. Examples of apparatuses that can be used for such washing treatment include the above-mentioned types of apparatus that can be used in acidification reaction treatment (e.g., mixer-settler, tube-type reactor). In a preferred embodiment, washing can be carried out continuously by countercurrent contacting an aqueous sulfuric acid solution as the aqueous phase with the reaction mixture, particularly the fluorocarboxylic acid phase, formed by the reaction. More specifically, washing may be carried out using an extraction column by feeding the aqueous sulfuric acid solution as the light liquid and the fluorocarboxylic acid phase as the heavy liquid, and inducing countercurrent contact between the two liquids. The operation may be carried out with the aqueous phase serving as the continuous phase, and the organic phase serving as the dispersed phase, or vice versa.

In the inventive process, sulfuric acid is present in both acidification reaction treatment and washing treatment, but the sulfuric acid is chemically consumed in the acidification reaction. Accordingly, in cases where the aqueous phase which forms in the acidification reaction is used in washing, acidification treatment is carried out in such a way that a given concentration of sulfuric acid remains present in the aqueous phase even after chemical consumption of the sulfuric acid has occurred. Moreover, because sulfuric acid is not consumed in washing treatment, in cases where the aqueous sulfuric acid solution obtained following use in washing is subsequently employed as the aqueous phase in acidification reaction treatment, washing treatment is carried out using an aqueous sulfuric acid solution that initially contains an excess amount of the sulfuric acid consumed by the acidification reaction. In the latter embodiment of the inventive process, the fluorocarboxylate acidification reaction can be carried out in the presence of the aqueous phase obtained after washing. This is particularly advantageous in cases where these washing and acidification reaction treatments are carried out continuously.

Specifically, (a) a sulfuric acid-containing aqueous phase and a fluorocarboxylic acid-containing fluorocarboxylic acid phase are obtained by liquid-liquid separation following washing, and the aqueous phase is utilized in the acidification reaction (the fluorocarboxylic acid phase can be used as finished product for a specific application); (b) next, the aqueous phase thus obtained and a fluorocarboxylate-containing aqueous solution are mixed and the acidification reaction is carried out, following which the reaction mixture is placed at rest, giving a fluorocarboxylic acid-containing organic phase (i.e., fluorocarboxylic acid phase) and an aqueous phase (the aqueous phase obtained contains sufficient sulfate, and so is discharged outside of the process system in which the inventive process is carried out); (c) the organic phase obtained is washed with fresh aqueous sulfuric acid solution, and liquid separation is effected after washing, giving a sulfuric acid-containing aqueous phase and a fluorocarboxylic acid-containing fluorocarboxylic acid phase. The aqueous phase is used in hydrolysis. Step (c) is the same as above step (a). By repeating steps (a) to (c), the washing treatment and acidification reaction treatment in the inventive process can be carried out continuously. Indeed, carrying out the inventive process in this way is preferred.

In this type of arrangement, a reaction apparatus (the apparatus of step (b)) which carries out acidification reaction treatment and a washing apparatus (the apparatus of step (a) or step (c)) which carries out washing treatment are each provided, and continuous operation may be carried out by continuously feeding the reaction mixture, and particularly the fluorocarboxylic acid phase, that arises from the acidification reaction treatment from the reaction apparatus to the washing apparatus, and continuously feeding the aqueous phase that arises from washing treatment from the washing apparatus to the reaction apparatus. However, in cases where the inventive process is employed on an industrial scale, it is preferable to carry out acidification reaction treatment and washing treatment continuously using a single apparatus.

It is especially preferable to use, as such a single apparatus, a countercurrent extraction column capable of continuously countercurrent-contacting the light liquid phase and the heavy liquid phase, and especially a countercurrent differential extraction column. Various extractors capable of countercurrent operation are known. Specific examples of such extractors that may be used include agitated plate-type extraction columns (e.g., rotary-disk extraction columns) and non-agitated plate-type extraction columns (e.g., perforated-plate extraction columns). Using such equipment, acidification reaction treatment and washing treatment can be continuously carried out by countercurrent contact between the organic phase and the aqueous phase.

An especially preferred type of extractor for carrying out the inventive process is an extraction column of the type sold by Sumitomo Heavy Industries Ltd. as a Karr column. Karr columns have a cylindrical section and receptacles which function as decanters and are positioned above and below the cylindrical section.

When the inventive process is carried out using this type of extraction column, the aqueous sulfuric acid solution is continuously fed as the light liquid from the bottom of the cylindrical section and forms an aqueous continuous phase which rises up through the entire column. The fluorocarboxylate-containing aqueous solution is continuously fed as the heavy liquid from the top of the cylindrical section. Feeding the fluorocarboxylate-containing aqueous solution to the extraction column and bringing it into countercurrent contact with aqueous sulfuric acid solution-containing aqueous phase rising up through the column causes the acidification reaction to proceed, as a result of which a fluorocarboxylic acid-containing organic phase forms and descends. Washing proceeds continuously by means of countercurrent contact between the organic phase and the aqueous phase. The acidification reaction arises at the vicinity of the fluorocarboxylate-containing aqueous solution feed opening to the extraction column. This zone is the reaction zone.

Some of the sulfate formed by the acidification reaction is taken up by the sulfuric acid-containing aqueous phase at the reaction zone near the feed opening, and the remainder is present in the fluorocarboxylic acid phase (organic phase). During the period that the organic phase descends through the column in the form of liquid droplets as the dispersed phase, it comes into countercurrent contact with the sulfuric acid-containing aqueous phase rising up as the continuous phase through the column. Such contact causes the transfer, or extraction, of sulfate present within the organic phase into the aqueous phase, thereby washing the fluorocarboxylic acid phase.

In cases where the fluorocarboxylate-containing aqueous solution serving as starting material contains other components which do not take part in the acidification reaction, such as hydrogen sulfide, such other components may also be present in the fluorocarboxylic acid phase. In the inventive process, such other components are at least partly removed from the fluorocarboxylic acid phase by washing. In this sense, when the starting material contains components capable of being taken up by the aqueous sulfuric acid solution, the inventive process can wash and thereby remove such components from the resulting fluorocarboxylic acid phase.

Conversely, in cases where the fluorocarboxylate-containing aqueous solution serving as the starting material contains other components which do not take part in the acidification reaction and which are not readily taken up by the aqueous sulfuric acid solution (e.g., a fluorocarboxylic acid), by being transferred to the fluorocarboxylic acid phase, such components can be included together within the fluorocarboxylic acid-containing fluorocarboxylic acid phase obtained from the acidification reaction. The fluorocarboxylic acid which may be included together in this way may be the fluorocarboxylic acid corresponding to the fluorocarboxylate being subjected to acidification treatment, or may be another fluorocarboxylic acid.

The above-described fluorocarboxylate acidification reaction and the washing of the fluorocarboxylic acid phase which contains the fluorocarboxylic acid formed as a result of the reaction are influenced by various equipment parameters that affect the extraction performance (e.g., length of the cylindrical section) and various operation parameters (e.g., flow rate of the fluorocarboxylate-containing aqueous solution supplied, and the concentration and flow rate of the aqueous sulfuric acid solution supplied). Generally, acidification of the fluorocarboxylate can achieve substantially 100% conversion in the presence of sufficient sulfuric acid. Removal (extraction efficiency) of sulfuric acid from the resulting reaction mixture, particularly the fluorocarboxylic acid phase, can be controlled by adjusting the above parameters. Those skilled in the art will be able to carry out the desired acidification treatment and washing treatment by setting the equipment and operation parameters to suitable values.

When the extraction column is operated as described above, the fluorocarboxylic acid phase (dispersed phase) following the removal of sulfate by the aqueous sulfuric acid solution accumulates and coalesces at the bottom end of the cylindrical section or in the bottom receptacle, forming a single fluorocarboxylic acid layer. Continuous removal of this fluorocarboxylic acid phase enables the fluorocarboxylic acid preparation process to be made continuous. The recovered fluorocarboxylic acid phase contains a small amount of impurities (e.g., water, sulfuric acid, sulfate). This amount is of a level which, depending on the intended use of the fluorocarboxylic acid, enables the simplification, and preferably the reduction, of subsequent purification treatment. Accordingly, the present invention provides a process for the continuous preparation of fluorocarboxylic acid, which process includes continuous acidification reaction treatment of the fluorocarboxylate and continuous washing treatment of the resulting fluorocarboxylic acid phase. More specifically, the invention provides a process for the preparation of fluorocarboxylic acid, which process includes an acidification reaction between a fluorocarboxylate-containing aqueous solution and sulfuric acid, and washing by countercurrent contacting an organic phase containing the fluorocarboxylic acid formed by acidification reaction with a sulfuric acid-containing aqueous phase.

As noted above, the inventive process for preparing fluorocarboxylic acid can be continuously carried out by using preferably a Karr extraction column. A Karr extraction column has numerous disk-like plates arranged within the cylindrical section of the extraction column. These plates can be moved vertically within the cylindrical section. By means of such vertical movement, the continuous phase and the dispersed phase are efficiently contacted within the cylindrical section, and the dispersed phase is efficiently coalesced and re-divided. Parameters that exert an influence on extraction by such an apparatus include, in addition to ordinary extractor parameters, the size of the vertically moving plates, the interval between neighboring plates, and the frequency of vertical movement. Suitable hydrolysis and washing can be carried out by adjusting these parameters.

The figure shows a flow sheet illustrating how the inventive process is carried out using this type of Karr column 10. The Karr column 10 is composed of a cylindrical section 12 and receptacles 14 and 16 positioned at the top and bottom ends thereof. Numerous disk-like plates 18 are arranged inside the cylindrical section. These are mounted on a shaft 20 at the center axis of the column. The shaft moves vertically in the manner indicated by the arrows A under the prompting of a motor 22 provided at the top of the column. The vertical movement by this shaft 20 causes the plates 18 to move up and down.

For example, a 30 wt % aqueous sulfuric acid solution ($H_2SO_4$ aq.) is supplied as the light liquid feed from the bottom end 23 of the cylindrical section 12 to the column 10, and fluorocarboxylate, such as the sodium salt of fluorocarboxylic acid (X—RfCOONa), is supplied as the heavy liquid feed to an upper portion 32 of the cylindrical section of the Karr column by a pump (the heavy liquid need not be fed in at the top end; as shown in the diagram, it may be fed in at a point somewhat downward from the top end). To ensure that acidification reaction treatment and washing treatment are carried out at a temperature higher than the melting point of the fluorocarboxylic acid, the temperature of the liquids that are fed to the column and the temperature of the liquids inside the column are controlled. In the illustrated embodiment, the aqueous sulfuric acid solution rises up through the column and forms an aqueous phase serving as the continuous phase. The fluorocarboxylic acid formed by the reaction forms an organic phase as the dispersed phase and descends through the column.

Upon entering the column, the fluorocarboxylate-containing aqueous solution that has been fed to the column is acidified in the presence of the sulfuric acid present therein, forming fluorocarboxylic acid (X—RfCOOH) and sulfate. This acidification reaction occurs in the vicinity of the fluorocarboxylate-containing aqueous solution feed opening 32 to the column. Hence, the vicinity of the feed opening in the column (the areas above and below) become the acidification reaction zone 24 where the reaction shown in the figure takes place. As is apparent from the description given above, the fluorocarboxylate is converted to fluorocarboxylic acid in the reaction zone 24, forming a dispersed fluorocarboxylic acid phase, which subsequently descends in the state of liquid droplets through a washing zone 26 located below the reaction zone 24. During this descent, the sulfate present in the fluorocarboxylic acid phase transfers (i.e., is extracted) to the aqueous phase, as a result of which the fluorocarboxylic acid phase is washed.

The fluorocarboxylic acid phase that descends through the column accumulates in the receptacle 16 and the liquid droplets coalesce, forming a single fluorocarboxylic acid phase, resulting in the formation of an interface 28 with the aqueous phase. The fluorocarboxylic acid phase is composed primarily of fluorocarboxylic acid, and contains substantially no sulfate. This fluorocarboxylic acid phase is removed as heavy liquid phase outflow, yielding fluorocarboxylic acid which contains substantially no sulfate. This fluorocarboxylic acid contains water and sulfuric acid dissolved therein. The sulfuric acid and/or water may be removed, depending on the intended use of the fluorocarboxylic acid. Removal of the water and sulfuric acid may be achieved by, for example, distillation treatment.

The aqueous sulfuric acid solution which rises up through the column washes the descending fluorocarboxylic acid phase in the washing zone 26, becoming in the process a sulfate-containing aqueous phase. It then enters the reaction zone 24, where it participates in the acidification reaction on the fluorocarboxylate, takes up some of the sulfate formed by the acidification reaction, then leaves the reaction zone and reaches receptacle 14. It then overflows from receptacle 14 as light liquid phase outflow, and is discharged from the column.

In cases where the fluorocarboxylate-containing aqueous solution also contains hydrogen fluoride, the hydrogen fluoride behaves in the same way as the sulfate, with most of it moving to the aqueous phase in the reaction zone 24 and the washing zone 26. Only a small amount of hydrogen fluoride is present in the fluorocarboxylic acid obtained from the receptacle 16. Accordingly, the inventive process, especially one in which reaction and washing are continuously carried out using an extraction column, can also remove such hydrogen fluoride when it too is present in the fluorocarboxylate-containing aqueous solution, and is thus particularly useful.

Moreover, in the inventive process, the fluorocarboxylate-containing aqueous solution may already contain fluorocarboxylic acid (this fluorocarboxylic acid may be one which corresponds with the acidification-reacted fluorocarboxylate, or may be one which does not correspond thereto). In such a case, this fluorocarboxylic acid is inert to the acidification reaction, and behaves in substantially the same way as the fluorocarboxylic acid that arises from acidification of the fluorocarboxylate. Accordingly, with regard to the fluorocarboxylic acid that is already present, in cases where this contains impurities (e.g., hydrogen fluoride) capable of being extracted by an aqueous sulfuric acid solution or an aqueous phase, the inventive process provides the advantage of being able to recover a mixture of the fluorocarboxylic acid formed by the acidification and the fluorocarboxylic acid originally present in the fluorocarboxylate-containing aqueous solution from which such impurities have been removed.

In another embodiment, the process for preparing fluorocarboxylic acid may be carried out batchwise, using, for example, an agitated batch reactor and a settler. Alternatively, at least one of the acidification reaction treatment and washing treatment may be carried out continuously as described above.

EXAMPLES

An example of the invention is described below. However, the present invention should not be construed as being limited thereto.

Example 1

Continuous Acidification Treatment and Washing Treatment

The Karr column extractor shown in the figure was used in this example. The column has a cylindrical section 12 (length, 3.0 m) of 2.5 cm diameter, above and below which are positioned receptacles 14 and 16 as decanters. At the interior of the cylindrical section, disk-like plates 18 (55 plates positioned at 5 cm intervals) are moved vertically so as to agitate the liquid within the cylindrical section.

An aqueous sulfuric acid solution (30 wt %) was continuously fed as the light liquid at a flow rate of 150 g/min from the vicinity of the bottom end 23 of the cylindrical section. An aqueous solution of $C_7F_{15}COONa$ (concentration, 10.0 wt %) was continuously fed as the heavy liquid at a flow rate of 150 g/min from a feed opening 32 provided at a position 0.6 m from the top end 30 of the cylindrical section.

The $C_7F_{15}COONa$ acidification reaction occurred continuously in the vicinity (reaction zone 24) of where the aqueous solution of $C_7F_{15}COONa$ was fed to the aqueous sulfuric acid solution serving as the continuous phase. As the $C_7F_{15}COONa$ serving as the heavy liquid was converted by the acidification reaction to $C_7F_{15}COOH$, it formed a fluorocarboxylic acid phase, which descended in the form of liquid droplets within the aqueous sulfuric acid solution.

Sodium sulfate formed by the acidification reaction was present in the fluorocarboxylic acid phase serving as the dispersed organic phase, but during descent of the fluorocarboxylic acid phase through the column, it was continuously extracted (i.e., washed) at the washing zone 26 by the aqueous sulfuric acid solution or aqueous phase rising up through the column. The liquid droplets of fluorocarboxylic acid phase (dispersed phase) that had descended coalesce in the decanter 16 at the bottom of the column and liquid separation occured, resulting in the formation of an interface 28 with the aqueous sulfuric acid solution.

The fluorocarboxylic acid phase that formed in the decanter 16 at the bottom of the column was recovered, and its composition was determined. The following results were obtained.

| | |
|---|---|
| $C_7F_{15}COOH$ | 95.5 wt % |
| $H_2O$ | 4.1 wt % |
| $H_2SO_4$ | 4,100 ppm by weight |
| Na ions | 3 ppm by weight |

The continuous phase (i.e., aqueous phase) in the decanter 14 at the top of the column was collected, and the $C_7F_{15}COOH$ concentration therein was analyzed. The concentration was 100 ppm by weight. Assuming that all of the $C_7F_{15}COONa$ supplied was acidified in the above-described acidification and washing operations, the percent recovery of $C_7F_{15}COOH$ was 99.9%.

It should further be apparent to those skilled in the art that various changes in form and detail of the invention as shown and described above may be made. It is intended that such changes be included within the spirit and scope of the claims appended hereto.

What is claimed is:

1. A process for preparing fluorocarboxylic acid in which acidification reaction treatment and washing treatment are continuously carried out, the process comprising:
   subjecting a fluorocarboxylate-containing aqueous solution to acidification reaction treatment in the presence of sulfuric acid so as to form a sulfate-containing fluorocarboxylic acid phase; and
   subjecting the fluorocarboxylic acid phase to washing treatment using an aqueous sulfuric acid solution,
   wherein said acidification and said washing are carried out at a temperature at which said fluorocarboxylic acid is a liquid.

2. The process of claim 1, wherein the fluorocarboxylate has the general formula

in which X is a hydrogen atom, a fluorine atom or a chlorine atom; M is a monovalent alkali metal or ammonium ion; and Rf is a linear or branched fluoroalkyl group of 4 to 14 carbons.

3. The process of claim 1, wherein the fluorocarboxylate has the general formula

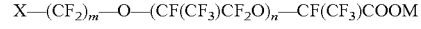

in which X is a hydrogen atom, a fluorine atom or a chlorine atom; m is an integer from 1 to 10; n is an integer from 0 to 5; and M is a monovalent alkali metal or ammonium ion.

4. The process of claim 1, which comprises maintaining an aqueous phase that is present in acidification reaction treatment at a sulfuric acid concentration of about 2 to 95 wt %.

5. The process of claim 1, which comprises carrying out the washing treatment in a liquid-liquid heterophase dispersed system composed of an aqueous phase and an organic phase, and maintaining the aqueous phase at a sulfuric acid concentration of about 2 to 95 wt %.

6. The process of claim 5, which comprises continuously carrying out the washing treatment by countercurrent contact between the organic phase and the aqueous phase.

7. The process of claim 1, which comprises continuously carrying out the acidification reaction treatment and washing treatment, using a differential contacting extraction column, by feeding the fluorocarboxylate-containing aqueous solution and the aqueous sulfuric acid solution to the extraction column so that they flow countercurrent to each other.

8. The process of claim 7, wherein the extraction column is a Karr column.

9. The process of claim 1, wherein the fluorocarboxylate comprises $C_7F_{15}COONa$.

10. The process of claim 1, wherein the fluorocarboxylate comprises $C_7F_{15}COONH_4$.

11. The process of claim 1, wherein M is selected from the group consisting of sodium, potassium and ammonium ion.

12. A process for preparing fluorocarboxylic acid in which acidification reaction treatment and washing treatment are carried out, the process comprising:
- subjecting a fluorocarboxylate-containing aqueous solution to acidification reaction treatment in the presence of sulfuric acid so as to form a sulfate-containing fluorocarboxylic acid phase; and
- subjecting the fluorocarboxylic acid phase to washing treatment using an aqueous sulfuric acid solution,
- wherein said acidification and said washing are carried out at a temperature at which said fluorocarboxylic acid is a liquid, and at least one of said acidification reaction treatment and washing treatment is carried out batchwise.

13. A process for preparing fluorocarboxylic acid in which acidification reaction treatment and washing treatment are carried out, the process comprising:
- subjecting a fluorocarboxylate-containing aqueous solution to acidification reaction treatment in the presence of sulfuric acid so as to form a sulfate-containing fluorocarboxylic acid phase; and
- subjecting the fluorocarboxylic acid phase to washing treatment using an aqueous sulfuric acid solution,
- wherein said acidification and said washing are carried out at a temperature at which said fluorocarboxylic acid is a liquid, and at least one of said acidification reaction treatment and washing treatment is carried out continuously.

* * * * *